United States Patent [19]

Webster, Jr. et al.

[11] 4,168,316
[45] Sep. 18, 1979

[54] IMMUNOSUPPRESSIVE-1-(THIOCAR-BAMOYL)-2-IMIDAZOLIDINONE

[75] Inventors: Leslie T. Webster, Jr., Shaker Heights; Kenneth S. Warren, Cleveland, both of Ohio

[73] Assignees: Northwestern University, Evanston, Ill.; Case Western Reserve University, Cleveland, Ohio

[21] Appl. No.: 884,074

[22] Filed: Mar. 6, 1978

Related U.S. Application Data

[63] Continuation-in-part of Ser. No. 645,728, Dec. 31, 1975, abandoned.

[51] Int. Cl.$^2$ .......................................... A61K 31/415
[52] U.S. Cl. .................................. 424/273 R; 424/99
[58] Field of Search .............................. 424/99, 273 R

[56] References Cited

PUBLICATIONS

Chemical Abstracts, vol. 86:150570a; 1977 citing Lucas et al., J. Immunol. 1977, 118 (2), pp. 418-422.
Daniels et al., The Journal of Immunology, vol. 115, No. 5, Nov. 1975, pp. 1414-1421.
Helv. Chem. Acta., vol. 49, pp. 2443-2452 (1966).
The Condensed Chem. Dictionary, 6th Ed., p. 395, Reinhold Pub. Corp., N.Y., May 4, 1964.

Primary Examiner—Donald B. Moyer
Attorney, Agent, or Firm—Sprung, Felfe, Horn, Lynch & Kramer

[57] ABSTRACT

By isolation and purification from the urine of patients treated with niridazole there is obtained substantially pure 1-(thiocarbamoyl)-2-imidazolidinone which exhibits marked immunosuppressive activity. A particular isolation procedure is described in addition to a chemical synthesis as follows:

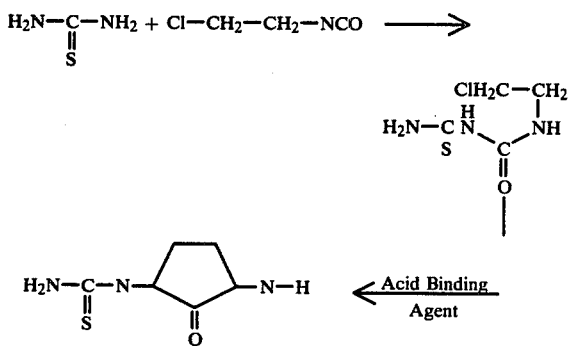

2 Claims, No Drawings

IMMUNOSUPPRESSIVE-1-(THIOCARBAMOYL)-2-IMIDAZOLIDINONE

This is a Continuation-in-Part application of Ser. No. 645,728, filed Dec. 31, 1975 now abandoned.

The present invention relates to the production of a new composition of matter of high immunosuppressive activity.

Niridazole, i.e. 1-(5-nitro-2-thiazolyl)-2-imidazolidinone has been employed widely as an anti-parasitic drug. An article by Mahmoud et al in Journal of Immunology Vol. 114 (1975) pages 279 ff reports on the discovery by the instant applicants that in patients undergoing prolonged treatment with niridazole there have been observed suppressed inflammations. Pursuing this, in tests on experimental animals niridazole administration has resulted in suppression of inflammation related to delayed hypersensitivity including retardation of allograft rejection. Human studies by Webster et al then corroborated the suppression of delayed hypersensitivity-type reactions by niridazole. It was speculated in both articles that the active material might have been a metabolite of niridazole rather than niridazole per se.

The instant applicants have since carried these researches further and have established that the active immunosuppressive agent is either a metabolite or is synthesized in the body in response to niridazole administration and they have provided processes whereby this active agent can be recovered, purified and concentrated, and compounded in a form suitable form administration. They have also provided a process for its chemical synthesis in the laboratory.

Specifically, they have found that the urine of mammals to which niridazole has been administered exhibit the desired immunosuppressive activity even long after the niridazole per se has been metabolized. They have therefore obtained the active material from the urine of mammals which have received niridazole by mixing the urine with an aqueous lower alkanol, separating solids from the liquid, drying said liquid, extracting said dried material with a lower alkyl ketone, drying the extract, subjecting the dried extract to chromatography, and collecting a fraction high in immunosuppressive activity.

Desirably the aqueous lower alkanol has a concentration of lower alkanol of about 30 to 70% by volume and is employed in about 50 to 200% by volume of the initial urine. Advantageously the lower alkyl ketone contains up to about 25% by volume of a lower alkanol, and/or other hydrophilic solvents, the dried material is subjected to a plurality of extractions with the lower ketone until substantially all the colored material is extracted from the dried material, and the extracts are combined and then dried. The dried extracts are then dissolved, preferably in water, the solution passed over a chromatographic absorbent and eluted with an aqueous acid, e.g. butanol: acetic acid: water. The eluate includes fractions of high immunosuppressive activity, e.g. at least about $2\Delta$ Log [Antigen] units as measured by the direct MIF assay, which fractions are suited for intravenous administration.

In the practice of the process there can be used mammals of all kinds ranging from humans to rats although for apparent reasons there are preferred large readily available, readily inexpensive mammals such as horses and livestock such as cattle, pigs and sheep.

The mammals can receive niridazole in about 25 to 100 mg/kg/day although they can receive larger doses so long as no adverse effects are observed. Smaller doses are also possible but may be less efficient. The decision will be based on the amount of active material produced, the cost of maintaining the animal and other economic factors.

Collection of urine can commence immediately upon administration of niridazole but generally at least one day is observed since appreciable quantities of the active immunospressive material do not show up for some time.

The urine from one or many mammals is collected to whatever volume is desired for processing and may be frozen so as to be processed at a later date upon thawing. Alternatively preservatives may be employed to maintain the activity of the urine even though kept at or near room temperature during storage. At any rate, prior to or immediately after storage the urine is advantageously treated, as in a centrifuge, to remove all solid material and the supernatant liquid concentrated by evaporation to near dryness.

The concentrate is mixed with about 50 to 200% based on the volume of the initial urine, of an aqueous lower alkanol. A 50% by volume solution of methanol in water is preferred, but other lower alkanols such as ethanol and isopropanol are also suitable and their concentrations can range from about 30 to 70% by volume. This serves to dissolve the active material so any undissolved residue can be discarded. Extraction can be effected at room temperature and by simple stirring although vigorous shaking for prolonged periods ensures more efficient recovery. Also higher or lower temperatures can be utilized.

The aqueous alcoholic solution is concentrated, preferably to dryness and preferably by lyophilization in which case the solid may be stored at about 4° C. prior to further processing. Thereafter the dried material is extracted with a lower alkyl ketone to remove all the colored matter from the solids which are discarded. The extraction with ketone is preferably employed in a series of stoages and it will be found that the ketone is discolored in the earlier stages. When a stage is reached where the extract is substantially colorless, further extraction can be discontinued. The lower alkyl ketone is preferably acetone but others such as batanol-2 are also suitable. The ketone as water, although preferably it contains up to about 25% by volume of a lower alkanol. A practical extraction has involved repeated extractions, e.g. 8, with acetone: methanol 10:1 by volume employed each time in about 25% by volume of the initial urine. The supernatants from the several extractions are combined, concentrated and lyophilized so they can be stored prior to further processing.

The dried extracts can then be dissolved, chromatographed and eluted with an aqueous acidic solution, separating the eluate into fractions of which those most active in immunosuppressive agent can be adjusted in composition to be suitable for application to patients where an immunosuppressive response is desired. Dissolution can be effected in water which can also contain organic solvents, e.g. butanol, acetic acid and the like, and the solutions passed over adsorbents such as hydroxypropylated dextran sold under the trademark Sephadex LH-20, cellulose such as Whatman 3 MM paper, and the like. The adsorbents are thereafter treated with eluants, such as acidified water and the eluate collected into fractions which are assayed for their activity. The active fractions of eluate can be lyophilized and the resulting solids made up to any concentrations, e.g. about 0.1 to 10 mg/ml, by dissolution in water, saline solution or other liquids suitable for administration.

Parallel processes carried out on the urine of the same species of mammals, and sometimes the identical mammals prior to niridazole-administration, not administered niridazole did not produce comparable immunosuppressive responses.

While the active material may be administered orally, the desired immunosuppressive effect will best be realized by administration intravenously in an amount corresponding to about $1 \times 10^{-2}$ to 10 mg/kg. Upon administration to mammals this suppresses delayed hypersensitivity as well as holding promise for minimizing rejections in tissue and organ transplants.

Comparable or even smaller doses of the chemically synthesized material can be similarly administered. It may be admixed with various solid or liquid diluents for oral administration, e.g. starch, carboxymethylcellulose, fructose, and the like, for the purpose of enlarging the mass of substance imbibed.

The MIF assay referred to hereinabove has reference to the "migration inhibitory factor" which the body produces and which production an immunosuppressive agent is supposed to block. The assay procedure employed is based on that described by David and David at page 249 of their "In Vitro Methods in Cell-Mediated Immunity" edited by Bloom et al (Academic Press, 1971). A capillary tube technique with modified Mackaness chambers was employed to measure the MIF activity resulting from the addition of various levels of OCB-BGG and get to peritoneal exudate cells (PEC) obtained from Hartley guinea pigs sensitized to this antigen. The culture medium was Eagle's Minimal Essential with penicillin (100 units/ml) and streptomycin (100μg/ml), and was made to contain 15% normal guinea pig serum. Chambers were incubated for 24 hours at 37° C. Areas of migration were projected, traced, and quantitated by planimetry, MIF production was expressed as percent inhibition of migration, calculated as:

$$\% \text{ inhibition of migration} = \left(1 - \frac{\text{area of migration in presence of antigen}}{\text{area of migration in absence of antigen}}\right) \times 100$$

Twenty percent or greater inhibition of migration usually represents significant MIF production by this assay according to the Student's t test. From the logarithm of the minimum concentration or antigen producing significant, i.e. >20%, inhibition of migration in the presence of active material there is subtracted the logarithm of the minimum antigen concentration needed to cause significant inhibition in the absence of added active material and the result is identified as Δ Log [Antigen]. The active material fractions produced in accordance with the present invention exhibit activities of at least about 2Δ Log [Antigen] units by these test procedures.

The invention will be further described in the following illustrative examples wherein all parts are by weight unless otherwise expressed.

EXAMPLE 1

(a) male Sprague Dawley rats, weighing from 250 to 600 grams, were placed in metabolic cages and maintained on a diet of Purina Rat Chow and water ad libitum. Control (pretreatment) urine was collected separated from feces from periods of up to one week. Volumes of 24-hour collections were measured and the urine was centrifuged for 10 minutes at 9000 g. The resulting supernatant was evaporated to near dryness in a rotary evaporator. The residues were stored at −8° C.

(b) The rats then received niridiazole orally by plastic tube or stainless steel cannula inserted into the esophagus; the dose was ~70 mg/kilo suspended in water. Twenty-four hour urine collections began after the initial niridazole dose and were continued for periods up to 6 weeks. Urine samples were processed and stored as described for the pretreatment control samples.

(c) The crude urine residues from (a) and (b) were repeatedly extracted by vigorous stirring for about 30 minutes in a volume of methanol-water (1:1) equivalent to the original urine volume. The suspension was centrifuged, the precipitate discarded and the supernatant solution evaporated, lyophilized and stored at 4° C. The lyophilized supernatant from the methanol-water extraction was stirred vigorously for 15 minutes in 8 successive portions of acetone-methanol (10:1) whereupon no yellow color was seen in the supernatant resulting from centrifugation of the mixture. Each portion of acetone-methanol was equivalent to 25% of the original urine volume. The supernatant solutions from each extraction were pooled, concentrated by evaporation, lyophilized and resulting powders were stored at −8° C.

(d) Approximately 200 mg portions of the lyophilized acetone-methanol supernatants were chromatographed on Whatman 3 MM paper in a butanol-acetic acid-water (10:3:5) ascending system for ~12–15 hours which time the solvent migrated about 35 cm. from the origin. Dried papers were viewed under short and long wave ultraviolet light and cut into 5 sections (Fractions I to V) according to differences observed between the chromatographic behavior of material prepared from niridazole-treated compared to the control animals. The fifth section (Fraction V) included material migrating near the solvent front, i.e., with Rfs from 0.7 to 1.0. Material was eluted from each section of paper in dilute acetic acid (pH 5) and lyophilized prior to assay. Material from Fraction V was rechromatographed in the same ascending system and divided into subfractions 1 through 5. Subfraction 3 was obtained from the middle of the visualized ultraviolet absorbing material. MIF activities of various fractions are shown in Table I.

TABLE I

Immunosuppressive Activity of Urine Fractions Separated by Solvent Extraction and Paper Chromatography from a Niridazole-Treated Rat

| Concentration of Urine Fraction in Culture Media (μg/ml) | Δ Log [Antigen] in Direct MIF Assay | | | | | |
|---|---|---|---|---|---|---|
| | Actone-Methanol Supernatant | Chromatogram Fractions | | | | |
| | | I | II | III | IV | V |
| 10 | 2 | 0 | 1 | 0 | 0 | 0 |
| 1 | 3 | 1 | 0 | 1 | 1 | 2 |
| 0.1 | 2 | 2 | 0 | 0 | 0 | 2 |
| 0.01 | 1 | 0 | 1 | 1 | 1 | 2 |
| 0.001 | 2 | 0 | 0 | 0 | 0 | 1 |

(e) Another 200 mg portion of lyophilized acetone-methanol supernatant form (c) was dissolved in water and chromatographed on a column (40×2.5 cm) of Sephadex LH-20, equilibrated and eluted with butanol-acetic acid-water (10:3:5) at a flow rate of about 40 ml/hour. The effluent was monitored at 254 nm and 3 ml fractions were collected. The most active fractions, centering on 150 ml, were pooled, evaporated and lyophilized residues were weighed prior to assay.

(f) Fractions from paper and Sephadex LH-20 chromatography, (d) and (e) respectively, were compared by ascending thin layer chromatography. This layer chromatography was carried out for 3-4 hours on Eastman 6064 cellulose strips in a butanol-acetic acid water (10:3:5) solvent system. The dried strips were viewed under ultraviolet light.

Different fractions were serially diluted in 10-fold logarithmic fashion in the culture employed for the direct MIF assay. The inhibition of migration of cells by antigen in such cultures was compared with that in media containing no added urine fraction. In each culture medium, four doses of OCB-BGG (1.0μ g/ml, 0.1μ g/ml, 0.01μ g/ml, and 0.001μ g/ml) were added to PEC from sensitized guinea pigs. Table II indicates the manner by which the direct MIF assay results were quantified to permit identification of immunosuppressive preparations. In the presence of Fraction I, OCB-BGG at three logarithmic dilutions (0.1μ g/ml, 0.01μ g/ml, and 0.001μ g/ml) failed to inhibit significantly the migration of PEC from guinea pigs sensitized to OCB-BGG. Compared with the control where no urine fraction was added, this represents a 3 log difference. By contrast, Fraction II produced only a one log difference from control, with 0.001μ g/ml OCB-BGG failing to inhibit migration. In order to be considered immunosuppressive, a urine fraction had to prevent inhibition of migration by at least 2 log doses of antigen compared to control. Therefore, Fraction I was immunosuppressive at the concentration tested whereas Fractions II was not

TABLE II

QUANTIFICATION OF IMMUNOSUPPRESSIVE ACTIVITY OF URINE FRACTIONS

| Antigen (OCB-BGG) μg/ml | Inhibition of Migration[a] | | |
|---|---|---|---|
| | Control | Fraction I 0.1 μg/ml | Fraction II 0.1 μg/ml |
| 1.0 | 61 | 36 | 51 |
| 0.1 | 44 | (10) | 58 |
| 0.01 | 46 | (4) | 25 |
| 0.001 | 33 | (−3) | (10) |
| Δ Log [Antigen] | | 3 | 1 |

[a]Values are percent inhibition of migration; 20% or greater is considered significant inhibition. Insignificant values are enclosed in parentheses.

The effect of urine fractions on granuloma formation around $S.$ $mansoni$ eggs injected intravenously into the pulmonary microvasculature was determined as described by Mahmoud et al in J. Immunology, Vol. 112 (1974) pages 222 ff. Groups of 5 weanling CF1 Swiss albino female mice (18–22 g body weight) obtained from Carworth Farms, Inc., New City, New York were treated by intravenous injection with different doses of urine fractions at varying time intervals before egg injection. Untreated mice and niridazole treated animals (1 mg/kg body weight given orally on the day before egg injection) were used as controls. Eight days after egg injection, the mice were killed and the average area of granulomatous inflammation around eggs in the lungs was determined with a μMC particle measurement computer system (Millipore Corp., Bedford, Mass.) as described by Mahmoud et al in J. Immunology, Vol. 114 (1975) pages 279 ff. Fifty granulomas containing eggs in their centers were measured from each experimental group and the significance of the difference was evaluated by the Student's t test. The results are given in Tables III and IV for the indicated chromatographic fractions.

TABLE III

In Vitro and In Vivo Immunosuppressive Activity of Paper Chromatogram Fraction V from Urine of a Niridazole-Treated Rat

| In Vitro | | In Vivo | | |
|---|---|---|---|---|
| Concentration of Fraction V in Culture Media (ng/ml) | Δ Log [Antigen] in Direct MIF Assay | Dose of Fraction V injected (μg/kg) | Mean Granuloma Area $(X \pm S.E.)$ $\mu^2 \times 10^3$ | |
| | | | Day −1[a] | Day −8 |
| 100 | 1 | 1000 | $9 \pm 1.3^{(b)}$ | $10 \pm 0.9^{(a)}$ |
| 10 | 2 | 100 | $9 \pm 1.1^{(b)}$ | $11 \pm 1.8^{(b)}$ |
| 1 | 1 | 10 | $10 \pm 1.7^{(b)}$ | — |
| 0.1 | 1 | 1 | $10 \pm 1.5^{(b)}$ | — |
| 0.01 | 0 | none Control | $18 \pm 2.8$ | $18 \pm 2.6$ |
| | | Fraction V (1 mg/kg) | $18 \pm 3.2$ | — |

[a]For comparison, niridazole administered orally in a single dose (1 mg/kg) on Day −1 produced a mean granuloma area of $11 \pm 2.6$ $\mu^2 \times 10^3$ (p<0.005).
[b]p<0.005 compared to control.
[c]Fraction V prepared from urine of the rat before it received niridazole

TABLE IV

In Vitro and In Vivo Immunosuppressive Activity of LH-20 Fraction I from Urine of a Niridazole-Treated Rat

| In Vitro | | In Vivo | |
|---|---|---|---|
| Concentration of Fraction I in Culture Media (ng/ml) | Δ Log [Antigen] In Direct MIF Assay | Dose of Fraction I injected (ug/kg) | Mean Granuloma Area $(X \pm S.E.)$ $\mu^2 \times 10^3$ |
| | | | Day −1[a]  Day −8 |
| 100 | 3 | 10 | $7 \pm 1.1^{(b)}$   $8 \pm 1.3^{(b)}$ |
| 10 | 2 | 1 | $7 \pm 1.2^{(b)}$   $10 \pm 1.1^{(a)}$ |
| 1 | 2 | 0.1 | $12 \pm 2.6$   $15 \pm 1.8$ |

TABLE IV-continued

In Vitro and In Vivo Immunosuppressive Activity of LH-20 Fraction I from Urine of a Niridazole-Treated Rat

| In Vitro | | In Vivo | | |
|---|---|---|---|---|
| Concentration of Fraction I in Culture Media (ng/ml) | Δ Log [Antigen] In Direct MIF Assay | Dose of Fraction I injected (ug/kg) | Mean Granuloma Area (X ± S.E.) $\mu^2 \times 10^3$ Day $-1^{(a)}$ | Day $-8$ |
| 0.1 | 2 | 0.01 | 15 ± 3.6 | — |
| 0.01 | 1 | none | 15 ± 1.6 | 16 ± 2.4 |
| 0.001 | 0 | Control Fraction I (100 μg/kg) | 13 ± 1.9 | 16 ± 2.0 |

[a]For comparision, niridazole administered orally in a single dose (1 mg/kg) on Day $-1$ produced a mean granuloma area of 8 ± 2.6 $\mu^2 \times 10^3$ ($p<0.005$).
[b]$p<0.005$ compared to control.
[c]$p<0.02$ compared to control.
[d]Fraction I prepared from urine of the rat before it received niridazole.

Table V shows the purification of immunosuppressive activity from urine of rats receiving niridazole. At each step, the specific activity was defined as the reciprocal of the lowest concentration of urine fraction at which significant activity could be detected. As can be seen, an approximate 100-fold purification of activity was achieved both by paper and LH-20 Sephadex chromatography.

TABLE V

Specific Activities of Immunosuppressive Fractions of Urine from Niridazole-Treted Rats

| Purification Stage | Lowest Suppressive Concentration[a] (ng/ml) | Specific Activity[b] | Fold Purification |
|---|---|---|---|
| Methanol—H₂O (1:1) Extraction | 10 | 0.1 | — |
| Acetone-Methanol (10:1) Extraction | 1 | 1 | 10 |
| Chromatography | | | |
| Paper Fraction V | 0.1 | 10 | 100 |
| LH-20 Fraction I | 0.1 | 0.1 | 100 |

[a]Based on direct inhibition of migration assay:
[b]Reciprocal of lowest concentration producing suppression.

The foregoing table and collateral trials show that extracts of rat urine obtained two days after niridazole administration (Day 2 extracts) at a concentration of 10 μg/ml suppressed inhibition of migration of 2 log unit of antigen concentration. The same concentration of Day 3 extract suppressed inhibition of migration by 3 log units. Neither lower concentration of both extracts nor similar extracts prepared from the urine of the same rats before niridazole treatment affected inhibition of migration. Also none of the precipitates remaining after extraction with methanol-water suppressed inhibition of migration.

A 10:1 acetone-methanol extraction of the active Day 3 sample resulted in a supernatant fraction and a residue fraction. The supernatant fraction at a concentration of 1 ng/ml suppressed inhibition of migration by 2 log units of antigen concentration. The residue fraction from this extraction procedure was not immunosuppressive, nor was the supernatant fraction from the extraction of control urine. Both supernatant and residue fractions were injected intravenously into mice. The residue fraction had no effect on granuloma formation but 10 mg/kg, 1 mg/kg, 0.1 mg/kg, and 0.01 mg/kg doses of the supernatant fraction all significantly suppressed granuloma formation ($p<0.005$) when they were given intravenously on the day before egg injection. Acetone-methanol supernatants prepared from urine of the animals before niridazole treatment had no effect on granuloma formation.

Table I indicates that immunosuppressive activity detectable at concentrations as low as 10 ng/ml in the MIF system was found in Fraction V of the paper-chromatogram located near the solvent front. Rechromatography on paper of this fraction yielded several ultraviolet bands, only one of which contained suppressive activity.

A "narrow cut" of the original Fraction V material eluted from the paper was divided into two portions, one for direct MIF assay and one for granuloma formation assay and the results of this comparison are shown in Table III. In the direct MIF assay, activity was detectable at concentrations as low as 10 ng/ml, but not lower. Granuloma formation in vivo was significantly suppressed at all doses of Fraction V tested, the lowest being 1 μg/kg on the day a "narrow cut" Fraction V fraction prepared from pretreatment control urine had no effect on granuloma formation.

Fraction I of the LH-20 chromatogram eluate near or at the void volume whereas Fractions II and III contained material eluting subsequently. Immunosuppressive activity was identified only in Fraction I by the inhibition of migration assay. Thin layer chromatography revealed that the LH-20 Fraction I and the paper chromatography Fraction V contained similar brownish colored material which migrated near the solvent front. The LH-20 Fraction I in the direct MIF assay indicated activity to a concentration of 0.1 ng/ml, but no lower. The granuloma assay indicated significant immunosuppression with the injection of as little as 1 μg/kg of the preparation on either the day before egg injection (Day-1) or on Day-8. Lower doses did not affect granuloma Formation. Doses of 1 μg/kg administered on Day-16 and Day-24 were also ineffective. Granuloma formation was not affected by an LH-20 Fraction I sample prepared from untreated control animals.

EXAMPLE 2

(A) Twenty-four hour urine samples were collected before and during drug therapy from a 24 year old white female patient with severe chronic graft vs. host reaction who received niridazole orally at 20 mg per kg body weight for 5 days. Urine collected without preservative was promptly frozen and stored, first at $-8°$ C. and later at $-70°$ C. Subsequently, the control pretreatment and 5th day niridazole treatment samples were thawed, centrifuged, the supernatants concentrated by evaporation to near dryness, and the resulting residues stored at −8° C.

(B) The product of (a) was processed as in Example 1 (b) (c) and (e) through the LH-20 fractionation stage. An LH-20 Fraction I sample was immunosuppressive at the lowest concentration tested, 1 ng/ml, in the direct MIF assay. Single dose of the same material at 1 μg/kg given on the day before egg injection strongly suppressed granuloma formation ($p < 0.005$ compared to control). An acetone-methanol extract of urine collected during the pretreatment, in control, period showed no immunosuppressive activity in the MIF assay.

When the product of the LH-20 fractionation step was subjected to high pressure liquid chromatography on a Waters Associates μBondapak C18 reverse phase column (0.4×30 cm) using a linear solvent gradient of 5% to 30% (v/v) acetonitrile in water, all of the immunosuppressive activity was confined to a single peak of uv-absorbing ($\lambda_{max} = 256$ nm) material. This information allowed the development of an improved purification procedure suitable for isolating milligram quantities of the immunosuppressive material from urine.

EXAMPLE 3

Twenty-four hour urine samples were quantitatively collected from two patients with mild *Schistosoma hematobium* infections who received niridazole orally in single daily doses of 25 mg/kg body weight for 7 days. The patients were in otherwise generally good health and showed normal liver function tests. Urine was collected without preservative and was promptly frozen at −20° C. and stored.

The process of the purification was monitored by analytical high pressure liquid chromatography (HPLC) on a Waters Associates μBondapak C18 reverse phase column (0.4×30 cm) with a linear flow program of 7% acetonitrile from 0.5 ml/minute to 2.0 ml/minute over a period of 10 minutes. The column effluent was monitored at 256 nm. Under these conditions at room temperature (25°), the immunosuppressive material had a retention time of 2.05±0.03 relative to water.

Three liters of urine containing approximately 1.4 μg of immunosuppressive material (NIF) per ml were thawed and concentrated to 600 ml by rotary evaporation at 30° C. The reddish-black precipitate which formed upon cooling to 4° C. was removed by centrifugation for 10 minutes at 10000×gmax at 0° C. NIF could not be detected in this precipitate. The 5-fold concentrated urine was extracted twice with an equal volume of ethyl acetate. The combined organic extracts were filtered through Whatman PS-1 phase separating paper and evaporated to dryness at 30° C. Greater than 93% of the NIF present in the concentrated urine was recovered by this procedure. Repeating the extraction a third time did not significantly increase the recovery of NIF, but did result in the extraction of considerable uv-absorbing material. The aqueous phase was discarded. The amber-colored residue from the ethyl acetate extract was taken up in 2.5 ml of water. A small amount of water-insoluble material, which contained no measureable NIF, was discarded.

The water-soluble material from the previous step was applied to a column of Sephadex G-25 fine (2.6×62 cm) which was equilibrated at 25° C. with 0.02% $NaN_3$. The column was developed with the same solvent, a flow rate of 69 ml/hour and a pressure of 30 cm water and 3.0 ml fractions collected. The column effluent was monitored at both 256 nm and 360 nm. The NIF content of individual fractions was determined by HPLC analysis of 5 μl aliquots.

Fractions from the first Sephadex G-25 column containing NIF were pooled and evaporated to dryness at 30° C. The residue was dissolved in 3.0 ml of water and applied to a second Sephadex G-25 column (2.6×62 cm). This column was developed with 0.02% $NaN_3$ as had been done with the first column. Again, fractions containing NIF were pooled and evaporated to dryness. HPLC analysis of the pooled fractions showed NIF to be the major 256 nm-absorbing component.

NIF was further purified by preparative HPLC on a Waters Associates μBondapak C18 column (0.79×30 cm), developed with 7% aqueous $CH_3CN$ at a flow rate of 2.0 ml/minute. The column effluent was monitored at 256 nm. Under these conditions, NIF eluted with a retention volume of 2.18±0.02 relative to water (water=1). The column effluent containing NIF was collected and the solvent was removed by rotary evaporation at 30° C. The white-colored residue was dissolved in 2.0 ml of water.

A second preparative HPLC step was included to remove minor contaminants and to minimize solvent impurities. The preparative μBondapak C18 column was washed with 10 column volumes of acetonitrile (Burdick-Jackson, uv-quality solvent) and then equilibrated with water which was highly purified by passage through a Milli-Q system (Millipore Corporation). When chromatography was done in water at a flow rate of 4.0 ml/minute, NIF eluted with a retention time of 21.6 minute. Again the column effluent was monitored at 256 nm and at the appropriate time, NIF was collected. The volume of the collected effluent was reduced to 4 ml by rotary evaporation at 30° C. NIF (3.19 mg) was recovered as a fine white powder after lyophilization. The final product was judged pure by analytical HPLC.

Overall, the immunosuppressive material was purified greater than 13,000-fold in a dry weight basis from the 5-fold concentrated urine and was recovered in a 74% yield. A summary of the purification is given in the accompanying table VII.

TABLE VII

Summary of Purification of Immunosuppressive Material (NIF) from Human Urine

| Step | Total NIF (mg) | Total Solids[b] (mg) | Overall Purification (Fold)[d] | Overall Recovery (%) |
|---|---|---|---|---|
| 5-fold Conc. Urine | 4.34[a] | 58200 | 1.0 | 100 |
| Ethyl Acetate Extract | 4.06 | 812 | 67 | 93 |
| First Sephadex G-25 Step | 3.78 | ND[c] | ND | 87 |
| Second Sephadex G-25 Step | 3.37 | ND | ND | 78 |
| Preparative HPLC in 7% $CH_3CN$ | 3.26 | ND | ND | 75 |
| Preparative HPLC in water | 3.19 | 3.19 | 13,400 | 74 |

[a]The total NIF content in the 5-fold concentrated urine was estimated from the amount of NIF extracted into ethyl acetate after four extractions with an equal volume of the organic solvent. The crude urine could not be assayed directly by HPLC because of interfering substances.
[b]Gravimetric determination after lyophilization.
[c]N.D. = not determined
[d]Based on the ratio of weight of NIF to weight of total solids compared to the 5-fold concentrated urine.

Electron impact mass spectroscopy gives a molecular ion m/e=145, with major fragments m/e=102, 43, 85, and 60.

Chemical ionization analysis gives a quasi-molecular ion, m/e=146.

In $D_2O$, employing nuclear magnetic resonance against $^1H$ the active material shows two apparent triplets of equal intensity whose chemical shifts closely resemble the resonances of the methylene protons of niridazole and 2-imidazolidinone.

In acetone-$d_6$, resonances corresponding to the three exchangeable amide protons were observed. As expected, these resonances were quite broad.

The uv-vis absorption spectrum shows a maximum absorption at 256 nm, a minimum absorption at about 240 nm and a high energy peak at 230 nm. The spectrum is nearly the same at pH 2, 7 or 11, with the exception that absorption in the region of 200–215 nm is decreased at pH 11.

It shows no absorption in the region of 360 nm, the wavelength of maximum absorption of nitrothiazole compounds.

The molar extinction coefficient at 256 nm was found to be $16,900 \pm 200$ $M^{-1} cm^{-1}$.

The same product can be prepared chemically according to the following reaction scheme:

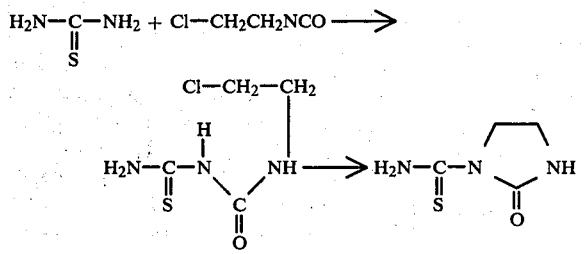

The starting materials react in a one-to-one stoichiometry, but advantageously thiourea is employed in excess, e.g. at least about six times the stoichiometric amount, to minimize substitution at the second free thioamide nitrogen. The reactions can be effected in water, water-miscible solvents such as lower alkanols, acetone and dioxane, or water-immisible solvents such as benzene or other hydrocarbons, chlorobenzene, and the like. The reaction temperature can be up to the boiling point of the solvent, if present, preferably at about 20° to 70° C. Ring closure can be effected with the aid of an alkaline acid-binding agent, e.g. alkali metal or ammonium hydroxide or carbonates or tertiary amines such as pyridine, trimethylamine, triethylamine, and the like. The by-product salt which forms is water soluble and in that manner can be separated from the desired product which can then be recrystallized from ethanol.

An illustrative process for preparation of the active material synthetically is shown in the following example:

EXAMPLE 4

To a solution of 19.0 g (250 nmol) of thiourea in 400 ml of acetone, containing 12.5 g (90 mmol) of anhydrous potassium carbonate, which was heated to 50° C., was added dropwise with stirring over a 90 minute period, a solution of 5.0 g (47.4 mmol) of 2-chloroethyl isocyanate diluted in 150 ml of acetone. The reaction mixture was stirred for two more hours at 50° C. After the insoluble carbonate was removed by filtration, the solution was evaporated to dryness at 45° C. under reduced pressure. The solids which remained were dissolved in 375 ml of N,N-dimethylformamide and heated to 94° C. Fourteen grams of sodium acetate trihydrate were added in one lot and the mixture stirred for 30 minutes at 94° C. After the solution had cooled to 45° C., the solvent was removed by rotary evaporation.

The solids were dissolved in 100 ml of water. Upon standing at 4° C., 1.8 g of crystals were deposited which contained approximately 90% by weight of a product which cochromatographed with the product from Example 3, when subjected to analytical high pressure liquid chromatography as in Example 3.

Recrystallization from 60 ml of water gave 1.44 g of white crystals which melted at 203.5° to 205.5° C. (uncorrected) and which was substantially free of thiourea. Traces of the starting material were removed by chromatography of the product in 250 mg lots on a Sephadex LH-20 (5×60 cm) which was developed with water. Under these conditions, thiourea eluted after about one bed volume of solvent had passed through, whereas the major product eluted after about two bed volumes.

Finally, highly purified product (~99% by weight) was obtained in milligram quantities by preparative high pressure liquid chromatography, using water as the solvent, as described in Example 3.

The chemically synthesized material had the same IR spectrum as the product of Example 3, with the following prominent features:

(1) Strong absorption bands of primary amide (N—H) stretching (3140 $cm^{-1}$ and 3320 $cm^{-1}$).

(2) A carbonyl (C=O) stretch at 1710 $cm^{-1}$ characteristic of 5 membered ring lactams.

(3) A primary amide (N—H) bending vibration at 1590 $cm^{-1}$.

(4) The presence of a strong absorption at 1093 $cm^{-1}$ in the region of 1250–1020 $cm^{-1}$ corresponding to C=S stretching vibration.

Chemical ionization, NMR, IR, UV, and electron spectroscopy indicate the material has the formula

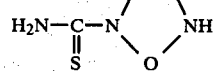

and is 1-(thiocarbamoyl)-2-imidazolidinone, which compound in Helv. Chem. Acta Vol. 49 (1966) pages 2443-6 is disclosed only as an intermediate in making other, structurally remote compounds of niridazole-like activity against schistosoma.

In further proof of the activity of the purified material from Example 3 as compared with niridazole per se, there was employed the ear swelling assay of Phanuphak et al. (1), which measures delayed-type contact sensitivity of inbred mice to 2,4-dinitro-1-fluorobenzene (DNFB). The assay was done according to the following protocol: on Day 1, groups of mice, matched for sex and weight, had their abdomens shaved and received varying doses of niridazole or NIF, the purified product of Example 2. The animals were sensitized on Day 3 with 20 $\mu l$ of 0.5% (v/v) DNFB in acetone: olive oil (4:1, v/v) applied to the shaved abdomen. The sensitization procedure was repeated on Day 4. On Day 8, mice were lightly anesthetized with ether and the right ear thickness measured ($10^{-2} \times mm$) by a modified dial thickness gauge. The right ear was then challenged with 10 μl of 0.5% DNFB solution. Twenty-four hours later, the mice were again anesthetized and the thickness of the right ear was measured to determine the immune response (swelling to the DNFB challenge).

The data from one niridazole experiment and two (NIF) experiments with urine isolated material are shown in Table 1. Significant suppression of ear swelling was obtained by $10^{-3}$ to $10^{-4}$ g/kg of niridazole given intraperitoneally. This can be compared with the extreme potency of pure (NIF) urine extracts where 50% suppression was seen with $10^{-8}$–$10^{-10}$ g/kg. It is clear from the data in experiment III that ear swelling was all but ablated at an extract dose of $10^{-12}$ g/kg. As yet it cannot be explained why less suppression is seen at higher doses of either niridazole (10 mg/kg) or extract $10^{-8}$ g/kg i.v.

TABLE VI

SUPPRESSION OF DNFB-INDUCED EAR SWELLING BY NIRIDAZOLE AND URINE EXTRACT

| EXPERIMENT NO. | MOUSE[a] STRAIN | NIRIDAZOLE DOSE | URINE EXTRACT DOSE (g/kg) | ROUTE | EAR SWELLING[b] ($10^{-2} \times$ mm ± SEM) | SUPPRESSION[c] (%) |
|---|---|---|---|---|---|---|
| I | F1 | 0 | — | — | 26.9 + 1.1 (5) | 0 |
|  | F1 | $10^{-3}$ | — | ip | 9.1 ± 1.2 (5) | 66 ± 4 |
|  | F1 | $10^{-2}$ | — | ip | 17.0 + 0.9 (5) | 37 ± 3 |
| II | F1 | — | 0 | — | 30.9 ± 6.8 (5) | 0 |
|  | F1 | — | $1.2 \times 10^{-10}$ | ip | 16.8 ± 1.2 (5) | 46 ± 4 |
|  | F1 | — | $1.2 \times 10^{-8}$ | ip | 16.0 ± 2.2 (5) | 48 ± 7 |
| III | B6 | — | 0 | — | 36.2 ± 0.8 (4) | 0 |
|  | B6 | — | $1.6 \times 10^{-12}$ | iv | 4.4 ± 3.2 (4) | 88 ± 9 |
|  | B6 | — | $1.6 \times 10^{-11}$ | iv | 12.8 ± 3.2 (4) | 65 ± 9 |
|  | B6 | — | $1.6 \times 10^{-10}$ | iv | 20.0 ± 4.3 (4) | 45 ± 12 |
|  | B6 | — | $1.6 \times 10^{-8}$ | iv | 27.2 ± 7.7 (4) | 25 ± 21 |
|  | B6 | — | $1.6 \times 10^{-10}$ | ip | 11.4 ± 4.8 (4) | 69 ± 13 |
|  | B6 | — | $1.6 \times 10^{-8}$ | ip | 17.5 ± 5.0 (4) | 52 ± 14 |

[a]B6=C57BL/6J; F 1=(C57BL/6J×DBA/2J) F1

It will be appreciated that the instant specification and claims are set forth by way of illustration and not limitation, and that various modifications and changes may be made without departing from the spirit and scope of the present invention.

What is claimed is:

1. An immunosuppressive composition of matter comprising water or saline solution as a pharmacologically acceptable diluent and an immunosuppressive effective amount of 1-(thiocarbamoyl)-2-imidazolidinone of the formula

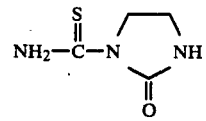

2. A method of suppressing an immunological response in a patient which comprises administering to such patient an immunosuppressive effective amount of 1-(thiocarbamoyl)-2-imidazolidinone of the formula

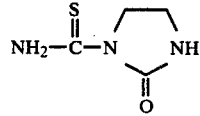

* * * * *

UNITED STATES PATENT AND TRADEMARK OFFICE
CERTIFICATE OF CORRECTION

PATENT NO. : 4,168,316
DATED : September 18, 1979
INVENTOR(S) : Leslie T. Webster, Jr. et al It is certified that error appears in the above-identified patent and that said Letters Patent are hereby corrected as shown below:

Title Page, In the Abstract:

Change 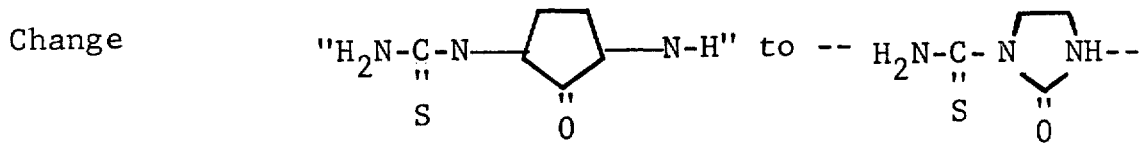

Column 12, line 45:

Change 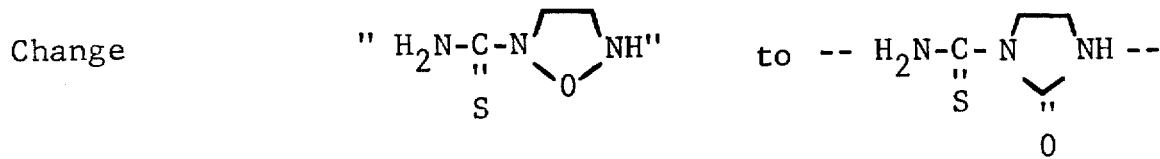

Signed and Sealed this

Twenty-seventh Day of May 1980

[SEAL]

Attest:

SIDNEY A. DIAMOND

Attesting Officer

Commissioner of Patents and Trademarks